US009775568B2

(12) United States Patent
Buresh, II et al.

(10) Patent No.: US 9,775,568 B2
(45) Date of Patent: Oct. 3, 2017

(54) MEDICAL DEVICE ALARM MANAGEMENT

(71) Applicant: Draeger Medical Systems, Inc., Andover, MA (US)

(72) Inventors: William T. Buresh, II, Salem, NH (US); Rajesh Rane, Andover, MA (US); Chung Wong, Framingham, MA (US); Hans Springensguth, Salem, MA (US)

(73) Assignee: Draeger Medical Systems, Inc., Andover, MA (US)

( * ) Notice: Subject to any disclaimer, the term of this patent is extended or adjusted under 35 U.S.C. 154(b) by 0 days.

(21) Appl. No.: 15/121,005

(22) PCT Filed: Feb. 24, 2015

(86) PCT No.: PCT/US2015/017301
§ 371 (c)(1),
(2) Date: Aug. 23, 2016

(87) PCT Pub. No.: WO2015/130674
PCT Pub. Date: Sep. 3, 2015

(65) Prior Publication Data
US 2016/0361030 A1 Dec. 15, 2016

Related U.S. Application Data

(60) Provisional application No. 61/945,702, filed on Feb. 27, 2014.

(51) Int. Cl.
*A61B 5/00* (2006.01)
*G06F 19/00* (2011.01)
(Continued)

(52) U.S. Cl.
CPC ............ *A61B 5/746* (2013.01); *A61B 5/7405* (2013.01); *A61B 5/7455* (2013.01);
(Continued)

(58) Field of Classification Search
CPC ..... A61B 5/746; A61B 7/7405; A61B 7/7455; G06F 19/0051; G08B 3/10; G08B 6/00; G08B 21/02; G08B 25/001; G08B 25/006
See application file for complete search history.

(56) References Cited

U.S. PATENT DOCUMENTS

| 5,153,827 | A | | 10/1992 | Coutré et al. |
| 5,920,263 | A | * | 7/1999 | Huttenhoff ......... A61B 5/02455 340/573.1 |

(Continued)

FOREIGN PATENT DOCUMENTS

| WO | 2008/150633 A2 | 12/2008 |
| WO | 2013/074769 A2 | 5/2013 |

OTHER PUBLICATIONS

International Electrotechnical Commission, "International Standard," IEC 60601-1-8, Edition 2.1, pp. 1-89, (2012).
(Continued)

*Primary Examiner* — Leon Flores
(74) *Attorney, Agent, or Firm* — Jones Day (57) ABSTRACT

It is determined, during monitoring of a patient, that a plurality of alarm conditions has been initiated. The alarm conditions characterize a measurement by and/or operation of at least one medical device and have an associated grade among a plurality of prioritized grades. Thereafter, alarms can be generated that corresponding to some or all of the plurality of alarm conditions such that among concurrent active alarms: (i) an alarm corresponding to an alarm condition having a highest priority grade is conveyed at a first level upon initiation and, if such alarm condition remains active for a pre-defined time period, at the first level upon expiration of the pre-defined time period, and (ii) alarms corresponding to alarm conditions having equal or lower priority grades than the priority grade of the current
(Continued)

highest priority grade alarm condition are conveyed at a second level, the second level being different from the first level.

20 Claims, 7 Drawing Sheets (51) Int. Cl.
| | |
|---|---|
| *A61M 16/00* | (2006.01) |
| *G08B 3/10* | (2006.01) |
| *G08B 6/00* | (2006.01) |
| *G08B 21/02* | (2006.01) |
| *G08B 25/00* | (2006.01) |

(52) U.S. Cl.
CPC ..... *A61M 16/0051* (2013.01); *G06F 19/3406* (2013.01); *G08B 3/10* (2013.01); *G08B 6/00* (2013.01); *G08B 21/02* (2013.01); *G08B 25/001* (2013.01); *G08B 25/006* (2013.01); *G06F 19/3481* (2013.01); *G06F 19/3487* (2013.01); *G08B 25/00* (2013.01)

(56) References Cited

U.S. PATENT DOCUMENTS

| | | | |
|---|---|---|---|
| 8,571,893 B2 | 10/2013 | Dashefsky et al. | |
| 2005/0242928 A1* | 11/2005 | Kirkeby | G08B 5/22 340/286.07 |
| 2008/0094227 A1* | 4/2008 | Becker | A61B 5/0002 340/573.1 |
| 2011/0080294 A1* | 4/2011 | Tanishima | A61B 5/1455 340/573.1 |

OTHER PUBLICATIONS

International Search Report and Written Opinion for Application No. PCT/US2015/017301, dated Jun. 18, 2015.

* cited by examiner

MEDICAL DEVICE ALARM MANAGEMENT

CROSS REFERENCE TO RELATED APPLICATIONS

The current application is a national stage application, filed under 35 U.S.C. §371, of International Application No PCT/US2015/017301, filed Feb. 24, 2015, which claims priority to U.S. Provisional Application No. 61/945,702 filed on Feb. 27, 2014, the contents of each of which are hereby fully incorporated by reference.

TECHNICAL FIELD

The subject matter described herein relates to the management of concurrent alarms from medical devices having different priority grades.

BACKGROUND

Operating room environments are using increasingly sophisticated medical devices (e.g., patient monitors, ventilators, anesthesia machines, physiological sensors, etc.) in connection with the care of patients. However, triggered alarms provided by such medical devices, some of which are clinically relevant and many of which are not clinically relevant, act to distract caregivers, especially during procedures requiring a high level of precision. For example, it is imperative that caregivers are precise when a patient is being prepared for intubation or being intubated, when the patient is being maintained for optimal conditions for surgery, and when the patient is being weaned from anesthesia. Continued and concurrent alarms can be very distracting, especially if the caregiver has to acknowledge or silence the alarm multiple times by interacting with the medical device instead of providing the care required by the patient. Furthermore, in some cases, caregivers tend to turn off the alarms completely or modify the alarm limits beyond the clinically relevant alarm violations which can sometimes be hazardous. On the other hand, caregivers need to be immediately alerted to an alarm condition that is clinically relevant to the patient so that appropriate therapeutic intervention can be provided to the patient.

SUMMARY

In one aspect, it is determined, during monitoring of a patient, that a plurality of alarm conditions have been initiated. The alarm conditions characterize a measurement by and/or operation of at least one medical device and have an associated grade among a plurality of prioritized grades. Thereafter, alarms can be generated that corresponding to some or all of the plurality of alarm conditions such that among concurrent active alarms: (i) an alarm corresponding to an alarm condition having a highest priority grade is conveyed at a first level upon initiation and, if such alarm condition remains active for a pre-defined time period, at the first level upon expiration of the pre-defined time period, and (ii) alarms corresponding to alarm conditions having equal or lower priority grades than the priority grade of the current highest priority grade alarm condition are conveyed at a second level, the second level being different from the first level.

In some variations, if the alarm condition having the highest priority grade is removed prior to the expiration of the pre-defined time period, an alarm corresponding to an alarm condition having a next highest priority grade is conveyed at the first level and, if such alarm condition remains active for a pre-defined time period, is conveyed at the first level upon expiration of the pre-defined time period.

Some or all of the priority grades can have a different alarm at the first level, while two or more priority grades have the same alarm at the second level.

The alarm can be one or more of an audio alert, a visual alert, or a vibrational alert.

The current subject matter can be implemented with a wide variety of medical devices including, for example, patient monitors, anesthesia delivery platforms, ventilators, and physiological sensors.

In some variations, the one medical device forms part of an alarm management system or is otherwise coupled to the alarm management system. The alarm management system can convey alerts generating from various medical devices and/or sensors coupled to the patient.

In some cases, the medical device can allow for a caregiver to initiate an alarm pause for a second predefined time period in response to user-generated input via the at least one medical device. When such an alarm pause is initiated, at least a portion of alarms initiated during the pre-defined time period can result in an attention alarm being conveyed to a caregiver. In addition, alarms initiated during the second pre-defined time period having alarm conditions at a priority grade above a pre-defined threshold can be conveyed to the caregiver at the first level while all other alarms are conveyed to the caregiver at the second level.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. The medical device and/or the alarm management systems can include or otherwise form part of the computing systems. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the current subject matter allows alarms on medical devices to behave in such a way that the caregiver has reduced interaction with the medical device when alarms are sounding which, in turn, allows them to provide increased focus on the patient. At the same time, the medical device provides the necessary vigilance/notification for a new alarm (which can be acted upon for relevancy in the form of a quick glance by the caregiver in a hands free fashion) without needing to touch the medical device silence button or alarm off button.

The details of one or more variations of the subject matter described herein are set forth in the accompanying drawings and the description below. Other features and advantages of the subject matter described herein will be apparent from the description and drawings, and from the claims.

DETAILED DESCRIPTION

The current subject matter relates to the management of alarms on medical devices. Such medical devices measure or otherwise characterize various parameters for a patient such as their vital signs and they additionally can characterize various operating parameters (e.g., battery life, pumping rate, etc.). Example medical devices include, but are not limited to, patient monitors, anesthesia delivery systems or platforms, ventilators, physiological sensors, and the like.

It will be appreciated that given the multiple alarms going off for different physiologic conditions in a perioperative care area (as well as other care areas), there is a need for clear distinction of new critical level alarms from lower grade alarms when alarms of various grades are being concurrently triggered. As will be described in further detail below, this distinction can be achieved by having any alarm that has a higher priority grade than the current priority alarm sound a distinctive audible burst tone (as the grade of the alarm) for that higher priority alarm. For example, an alarm for heart rate limit violation having a medium priority grade can be first triggered followed by a high priority grade alarm for pulse oximetry desaturation. The desaturation alarm can sound one burst tone of a high grade in order to alert the user of the critical condition. Any alarms of same or lower priority will provide notification of a lesser urgency; subsequent audio notification of the same or lesser grade alarms can be identified with an attention alarm. With multiple alarms triggered and active, additional alarms at the same grade can be indicated by an attention alarm providing a separation between the first same priority grade alarm condition and the second same priority grade alarm condition. With the previous example, if another medium grade alarm such as end tidal carbon dioxide limit violation is triggered (rather than a pulse oximetry desaturation), only an attention alarm will sound as there is already a medium priority grade alarm condition active.

Figure 1:
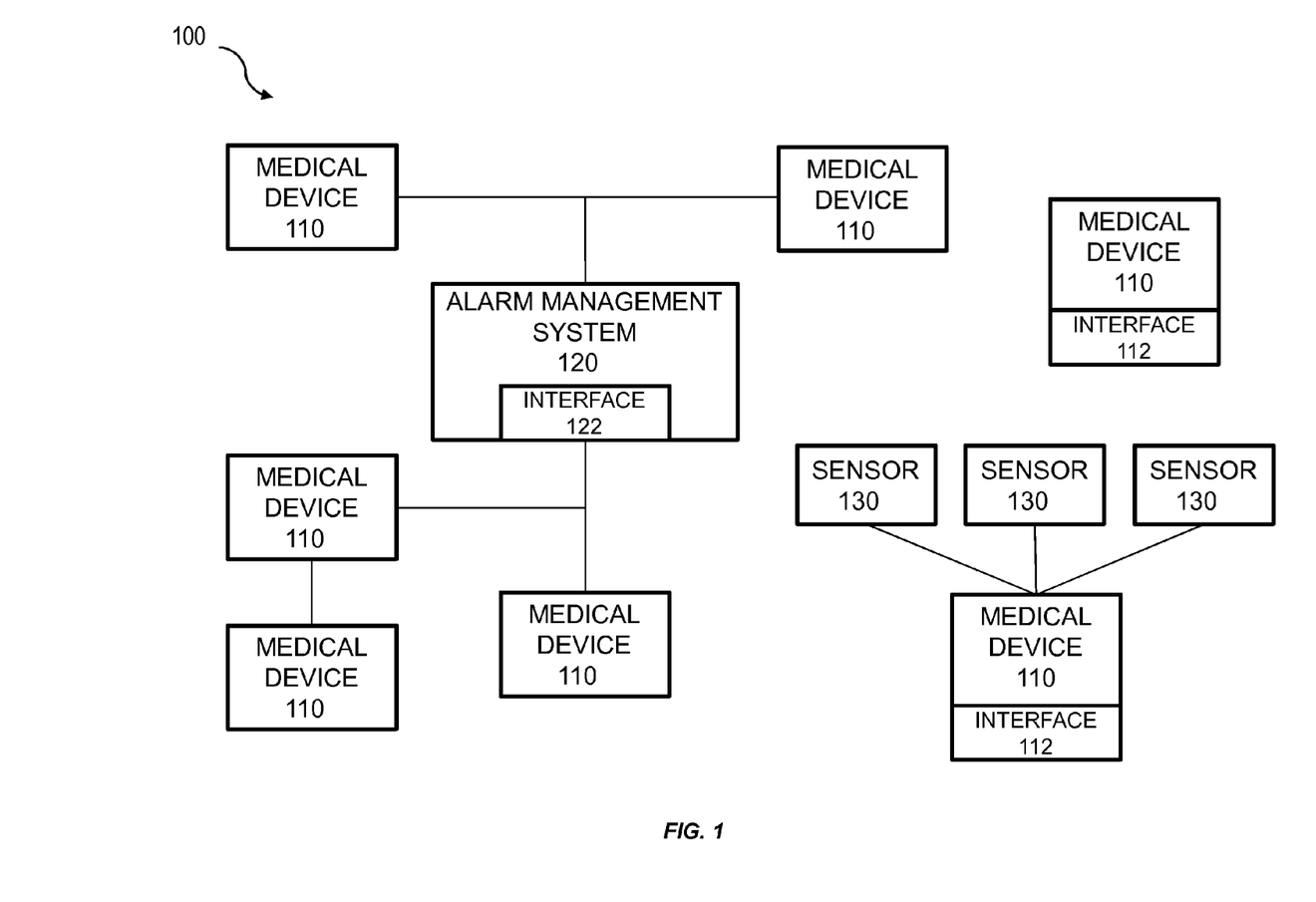
FIG. 1 is a system diagram illustrating a plurality of medical devices interfacing with an alarm management system.

With regard to diagram 100 of FIG. 1, in some cases, the alarms originate from a single medical device 110 while in other cases, the alarms can originate from two or more medical devices 110. With the latter arrangement, as show in diagram 100 of FIG. 1, multiple medical devices 110 can be coupled directly or indirectly (via a different medical device 110) to an alarm management system 120. Such coupling can be via fixed hardwired connections or wireless and can comprise hardware and/or software interfaces. For example, one or more of the medical devices 110 can include an application programming interface (API) to pass data characterizing alarms to the alarm management system 120 and to allow a caregiver to view and/or silence alarms and/or modify alarms via the alarm management system 120 (which can be remote from the corresponding medical device 110). In some cases, the wireless connection allows for peer-to-peer direct coupling between a medical device 110 and the alarm management system 120, while in other cases, the medical device 110 and the alarm management system 120 interact via a computer network such as via a web service accessible over the Internet. Each medical device 110 can include an interface 112 for conveying alarms to caregivers. In some cases, the medical device 110 may not include an interface but rather such medical device can utilize the interface 112 of another medical device or an interface 122 of the alarm management system 120. The interfaces 112, 122 can include any mechanism for conveying information to a caregiver including, for example, display screens (e.g., touch screens, etc.), lights (e.g., LED lights, etc.), speakers, vibrational elements, and the like.

In some cases, the alarm management system 120 can form part of another medical device (such as a patient monitor coupled to various physiological sensors attached to a patient). For example, the alarm management system 120 can be implemented in software executed by a processor of a medical device. In addition, medical devices 110 can be coupled to one or more sensors 130 that, in turn, characterize aspects of a patient being monitored (e.g., vital signs, etc.).

The user interfaces 112, 122 can convey alarms to caregivers in the form of an audio and/or visual alert (or in some cases a vibrational alert). Unless otherwise specified, the term alert should be construed as including any manner to provide a notification to a caregiver. These alarms can be generated in response to alarm conditions being triggered as determined by the corresponding medical device 110, or in some cases, as determined by the alarm management system 120. These alarm conditions can be triggered, for example, when a measurement taken by the medical device 110 falls outside a pre-defined range and/or when one of the operating parameters of the medical device 110 falls outside a pre-defined range (e.g., remaining battery life, etc.).

While the following is described in relation to audio-based alarms, it will be appreciated that the current subject matter can also be applied to other types of alarms including visual and vibrational, and combinations thereof. In addition, as noted above, the current subject matter can be implemented directly on a medical device and/or it can be implemented using an alarm management system. For simplicity of the following narrative, reference will be made to audio alarms being presented on a medical device.

There can be various prioritized grades of alarms. For example, there can be a low priority tone, a medium priority tone, and a high priority tone with such tones being differentiated based on a number of corresponding notes/tones played in a short sequence. It will be appreciated that other mechanisms for differentiating alarms can be utilized (e.g., varying pitch, time intervals, etc.). In addition, there can additionally be an attention tone which can, as will be described in further detail below, be conveyed to a caregiver regardless of the corresponding priority grade of such alarm.

Figure 2:
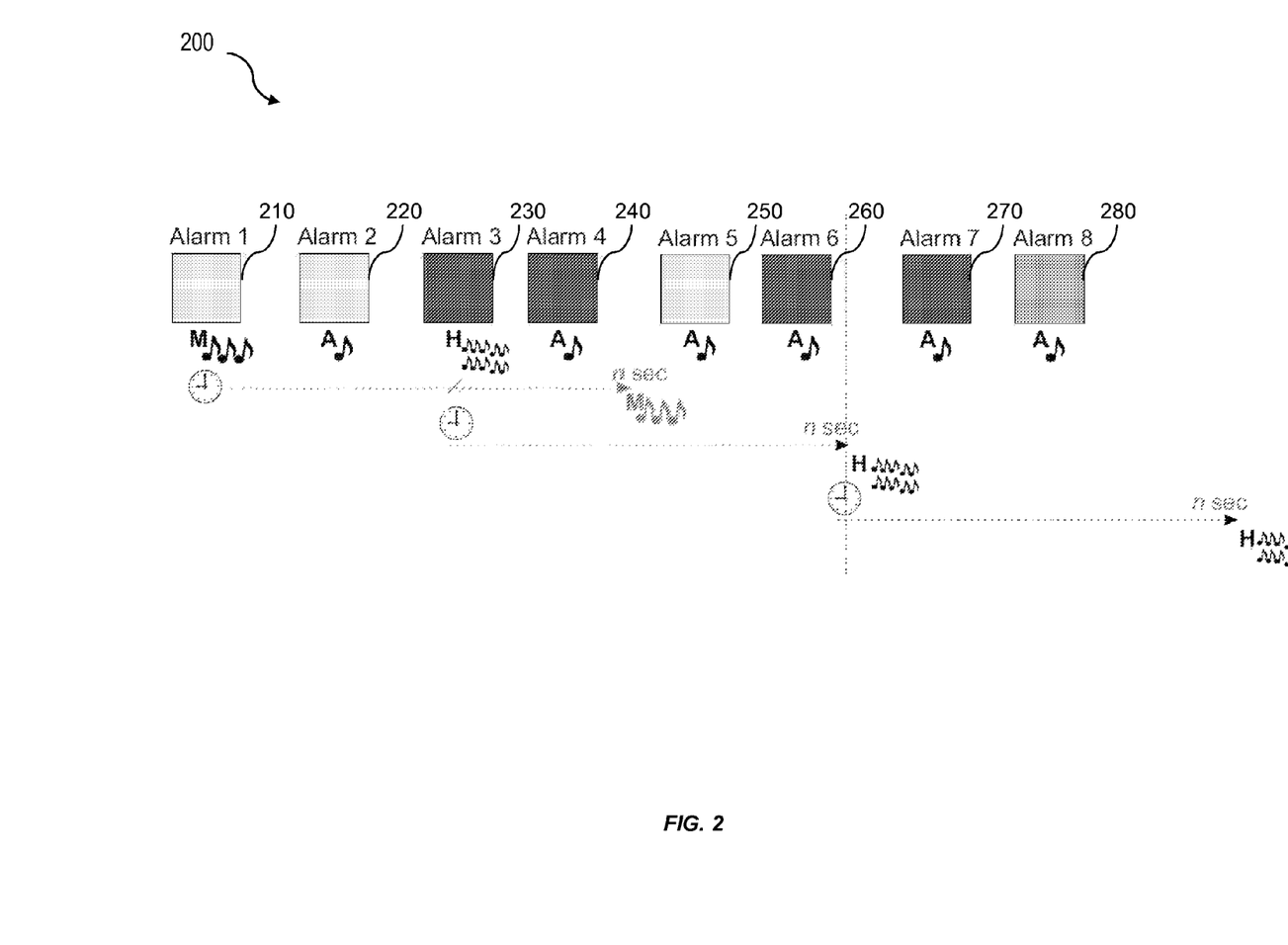
FIG. 2 is a diagram illustrating a first sequence of medical device alarms.

FIG. 2 is a diagram 200 illustrating a temporal progression of alarms. At 210, a first alarm having a medium priority grade is initiated by a corresponding alarm condition and conveyed to the caregiver via a pre-defined audio alert causing a timer to be initiated. The timer extends for a fixed period of time (e.g., 30 seconds, etc.) unless some intervening event occurs or the corresponding alarm condition for the alarm is removed. Subsequently, at 220, a second alarm is initiated that has a same priority grade (i.e., a medium priority grade) as the first alarm. Instead of the second alarm being conveyed to the caregiver as a series of notes (as with the first alarm), an attention alarm is conveyed to the caregiver. The attention alarm can be any variety of audio, visual, and/or vibrational cues to a user, provided that such cues are distinguishable (e.g., quieter, shorter, etc.) than other alarms (however in some cases a low priority alarm can be the same as an attention alarm) in order to minimize distraction to the caregiver. While the timer for the first alarm remains active, at 230, a third alarm having a high priority grade is initiated which results in a corresponding audio alert to be conveyed to the caregiver and the timer to be reset. Diagram 200 illustrates that, absent the occurrence of the third alarm, the first timer would have terminated and the medium priority alarm would have repeated. While the timer for the third alarm remains active, at 240, a fourth alarm corresponding to a high priority grade is initiated. As the active timer already pertains to a high priority grade, an attention alarm is conveyed to the caregiver and the timer is not reset. At 250, a fifth alarm having a medium priority is initiated causing an attention alarm to be conveyed to the caregiver (because it has a lower priority than the third alarm that initiated the current timer). At 260, a sixth alarm having a high priority is initiated also causing an attention alarm to be conveyed to the caregiver (because it has the same priority as the third alarm that initiated the current timer). Subsequent to the sixth alarm, the timer corresponding to the third alarm expires causing a high priority alarm to be conveyed to the caregiver (because a high priority alarm still remains active). At 270, a seventh alarm is initiated that has a high priority which causes an attention alarm to be conveyed to the caregiver (because a high priority alarm still remains active). At 280, an eighth alarm is initiated that has a low priority which causes an attention alarm to be conveyed to the caregiver (because a high priority alarm still remains active). Thereafter, the current timer expires causing a high priority alarm to be conveyed to the caregiver.

Figure 3:
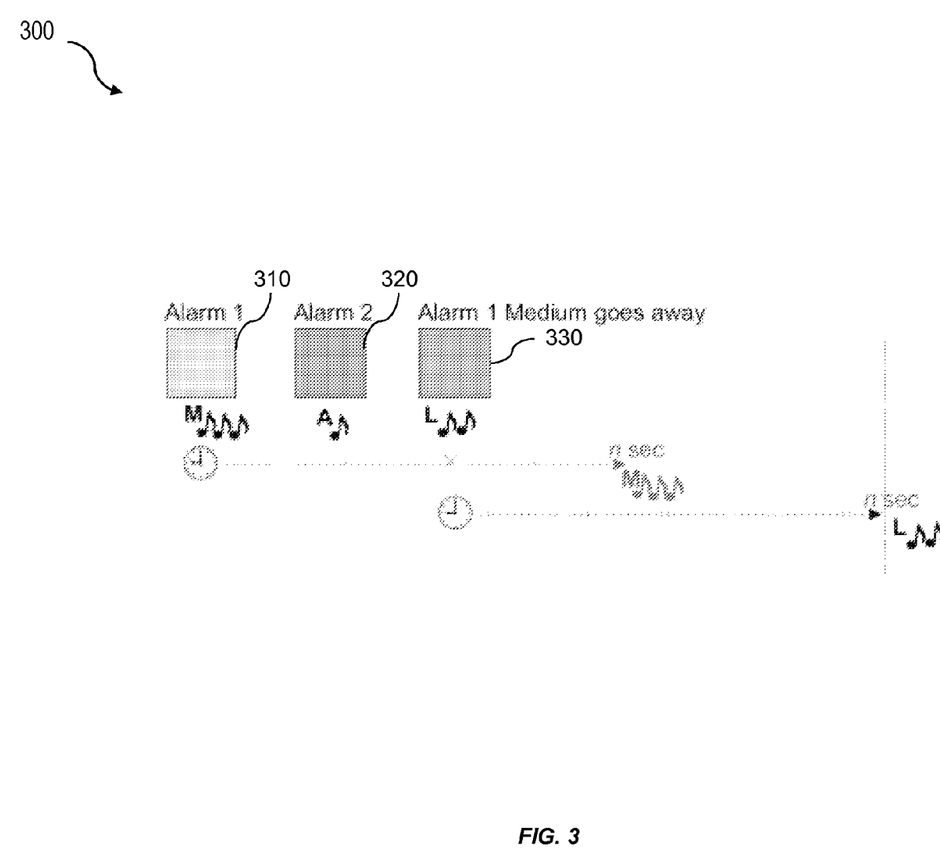
FIG. 3 is a diagram illustrating a second sequence of medical device alarms.

FIG. 3 is a diagram 300 illustrating a different sequence of alarms. At 310, a first alarm is initiated having a medium priority grade and a corresponding timer is initiated. Thereafter, at 320, a second alarm is initiated having a low priority which results in an attention alarm being conveyed to the caregiver. Prior to the timer for the first alarm expiring, at 330, the first alarm trigger condition is removed causing the first alarm to be removed. This removal results in a new timer being initiated that terminates with a low grade alarm being conveyed to the user upon its expiration (because the priority grade corresponding to the highest active alarm at such time is low grade).

Figure 4:
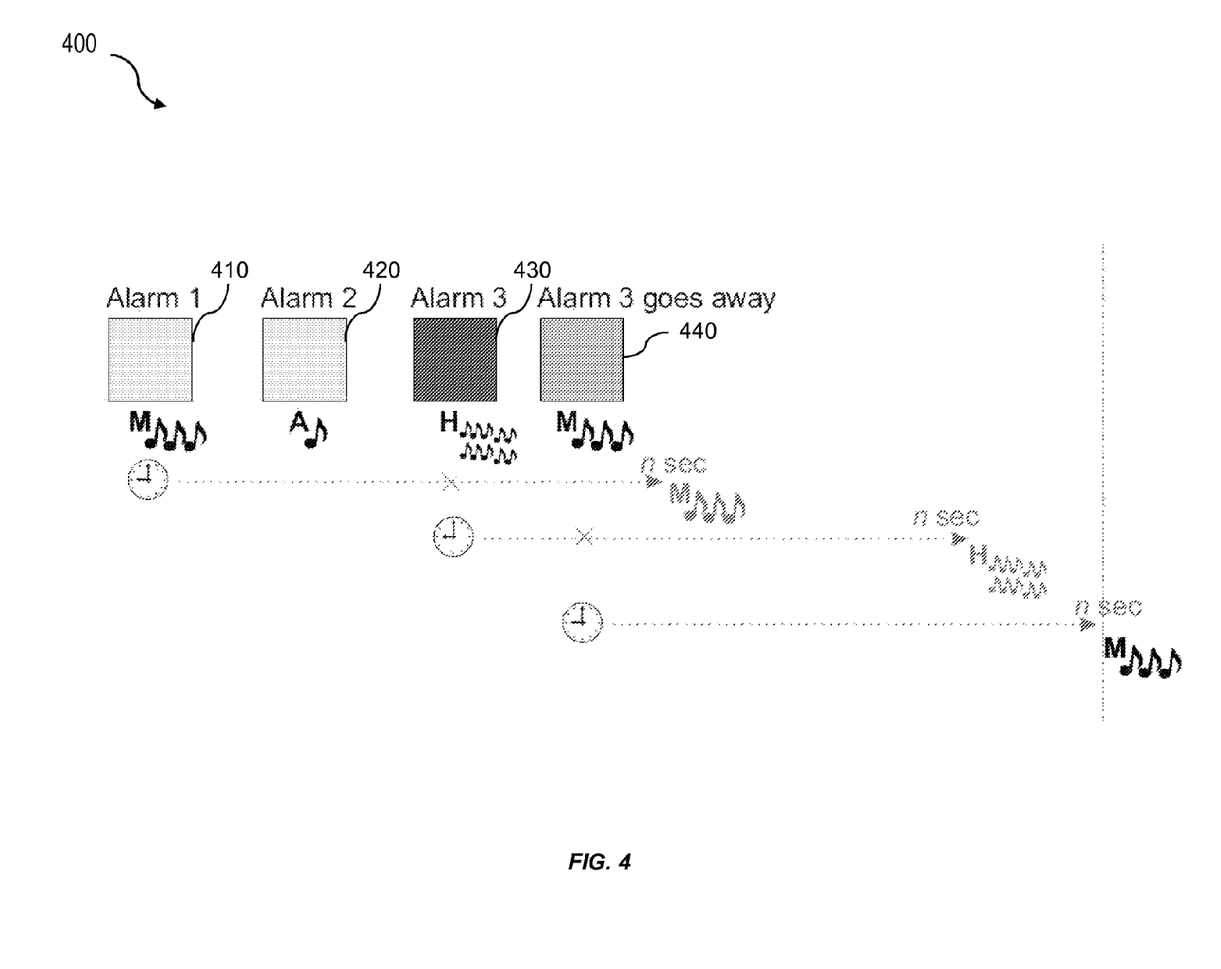
FIG. 4 is a diagram illustrating a third sequence of medical device alarms.

FIG. 4 is a diagram 400 illustrating yet another sequence of alarms. At 410, a medium priority grade alarm is initiated and conveyed to the caregiver. In addition, a corresponding timer is initiated at such time. While this timer remains active, at 420, a second alarm of medium priority grade is initiated which results in an attention alarm being conveyed to the caregiver. Again, while the timer corresponding to the first alarm remains active, at 430, a third alarm of high priority grade is initiated which results in a high priority grade alarm being initiated and the timer being reset. Before the expiration of the timer, at 440, the third alarm is removed which causes a medium priority grade alarm to be conveyed to the caregiver both when the third alarm is removed and at the expiration of such timer (because the priority grade corresponding to the highest active alarm at such time is medium grade).

Figure 5:
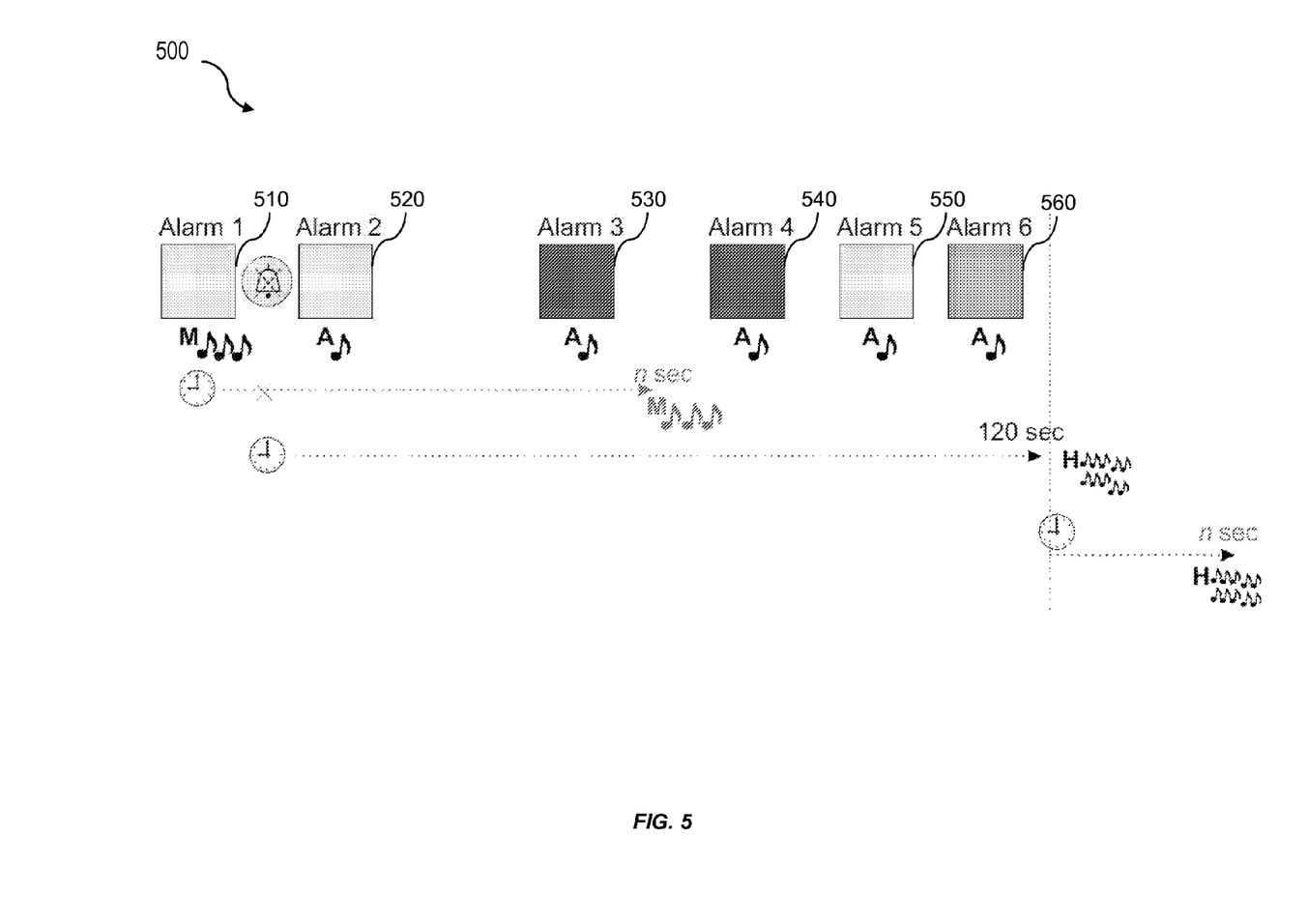
FIG. 5 is a diagram illustrating a fourth sequence of medical device alarms.

FIG. 5 is a diagram 500 illustrating a further sequence of alarms. At 510, a first alarm is initiated having a medium priority grade. In addition, a timer (e.g., a 30 second timer) is also initiated at such time. Subsequent to the first alarm, a caregiver can intervene by initiating an alarm pause (for example, via an interface element on a medical device or alarm management system). The alarm pause can result in some or all alarms during a pre-defined time period (e.g., 120 seconds, etc.) to be reduced such as by being muted, quieter, shorter, and the like. In some cases, all alarms initiated during the pre-defined time period are affected while in other cases only those alarms below a pre-defined threshold are affected (e.g., only medium priority grade alarms and lower are affected, etc.).

Continuing with one example, the alarm pause can result in a muting of the first alarm for a pre-defined time period (e.g., 120 seconds, etc.). During the audio pause timer, each new alarm initiated at 520-560 results in an attention alarm regardless of whether the priority grade is higher or lower than the first alarm. Upon the expiration of the audio pause timer, an alarm is conveyed to the caregiver corresponding to the currently active alarm having the highest priority grade (in this case a high priority grade alarm).

Figure 6:
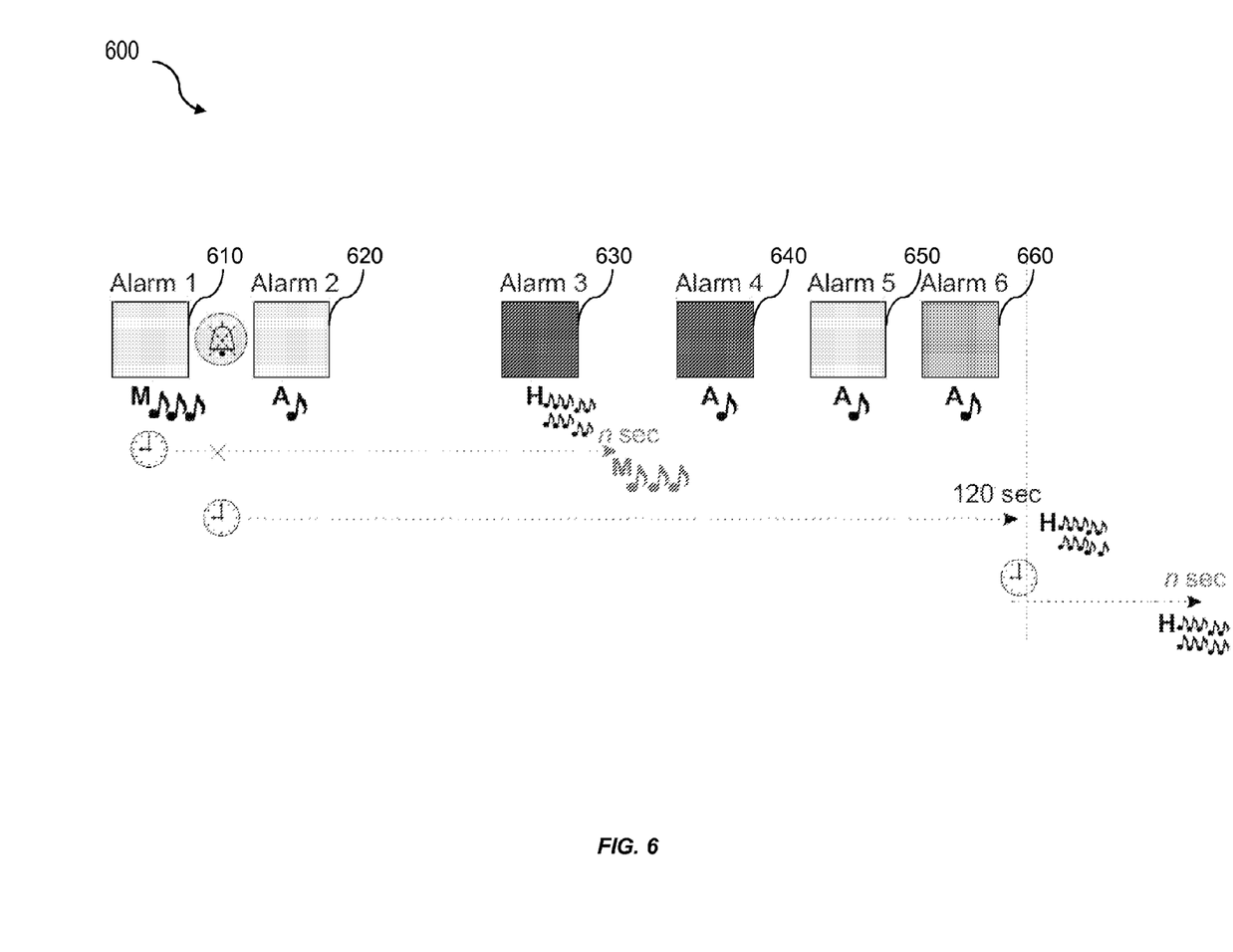
FIG. 6 is a diagram illustrating a fifth sequence of medical device alarms.

FIG. 6 is an additional diagram 600 illustrating a variation of FIG. 5 in which, at 610, a first alarm is initiated having a medium priority grade. In addition, a timer (e.g., a 30 second timer, etc.) is also initiated at such time. Subsequent to the first alarm, a caregiver intervenes by activating an audio pause (for example, via an interface element on a medical device or alarm management system). The audio pause results in a muting of the first alarm for a pre-defined time period (e.g., 120 seconds, etc.). During the audio pause timer, a second alarm, at 620, results in an attention alarm being conveyed to the caregiver. Subsequently, at 630, a third alarm having a high priority grade is initiated which results in a high alarm (as opposed to an attention alarm as in FIG. 5) being conveyed to the caregiver. Thereafter, each subsequent alarm at 640-660 results in an attention alarm regardless of whether the priority grade is higher or lower than the first alarm. Upon the expiration of the audio pause timer, an alarm is conveyed to the caregiver corresponding to the currently active alarm having the highest priority grade (in this case a high priority grade alarm).

While the above describes a particular arrangement in which all alarms having a same or lesser priority grade are conveyed using a uniform attention alarm, it will be appreciated that multiple type of attention alarms can be used. In addition, it will also be appreciated that some types of alarms having a lower priority grade can be conveyed using the corresponding default alarm or other type of alarm depending on the desired configuration.

Figure 7:
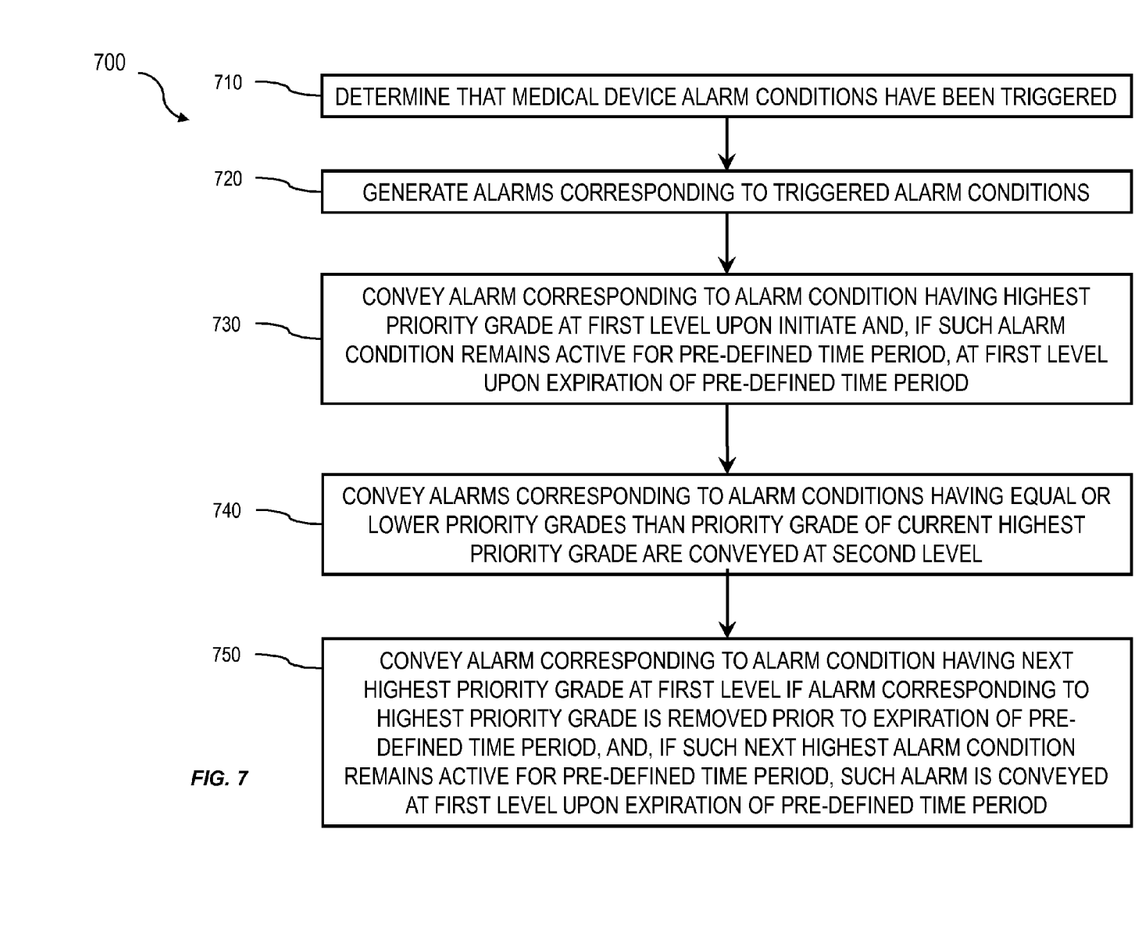
FIG. 7 is a process flow diagram illustrating generation of concurrent alarms derived from one or medical devices.

FIG. 7 is a process flow diagram 700 in which, at 710, it is determined during monitoring of a patient, that a plurality of alarm conditions has been initiated. Each alarm condition characterizes a measurement by and/or operation of at least one medical device and each alarm condition has an associated grade (e.g., high, medium, low, etc.) among a plurality of prioritized grades. Subsequently, at 720, alarms are generated that correspond to each of the plurality of alarm conditions. These alarms are generated such that among concurrent active alarms, at 730, an alarm corresponding to an alarm condition having a highest priority grade is conveyed at a first level upon initiation and, if such alarm condition remains active for a pre-defined time period, is conveyed at the first level upon expiration of the pre-defined time period, at 740, alarms corresponding to alarm conditions having equal or lower priority grades than the priority grade of the current highest priority grade are conveyed at a second level, the second level being conveyed at a level lower than the first level, and, at 750, optionally, if an alarm corresponding to the alarm condition having the highest priority grade is removed prior to the expiration of the pre-defined time period, an alarm corresponding to an alarm condition having a next highest priority grade is conveyed at the first level and, if such alarm condition remains active for a pre-defined time period, at the first level upon expiration of the pre-defined time period.

The following describes example percentage reduction in audio alarm tones during a surgical procedure with a single continuous alarm lasting four hours.

For Medium Priority Alarms (Conventional Arrangement):

Each individual alarm has 3 beeps which repeat every 6 seconds. Therefore, every 1 minute there are 3×10=30 beeps/minutes=30×60=1800 beeps/hour=1800×4 hour procedure=7200 beeps per procedure. With this conventional scenario, if the audio pause duration is set to 2 minutes, the user needs to interact with the medical device every 2 minutes to silence the audio alarm.

For High Priority Alarms (Conventional Arrangement):

Each individual alarm has 10 beeps which repeat every 5 seconds. Therefore, every 1 minute, there are 10×12=120 beeps/minute=120×60=7200 beeps/hour=7200×4 hour procedure=28,800 beeps per procedure. With this conventional scenario, if the audio pause duration is set to 2 minutes, the user needs to interact with the medical device every 2 minutes to silence the audio alarm.

For Medium Priority Alarm (Current Arrangement):

Each alarm has 3 beeps which repeat every 30 seconds. So every 1 min., there are 3×2=6 beeps/minute=6×60=360 beeps/hour=360×4 hour procedure=1440 beeps per procedure. With this scenario as implemented as described herein, the caregiver may not need to silence any alarms as they are less frequent and obtrusive.

For High Priority Alarm (New Situation):

Each alarm has 10 beeps which repeat every 30 seconds. So every 1 minute, there are 10×2=20 beeps/minute=20×60=1200 beeps/hour=1200×4 hour procedure=4800 beeps per procedure. With this scenario as implemented as described herein, the caregiver may not need to silence any alarms as they are less frequent and obtrusive.

As can be seen above, by implementing the current subject matter, an 83% reduction of high priority alarms and/or an 80% reduction of medium priority alarms can be realized for a four hour procedure.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (sometimes referred to as a computer program product) refers to physically embodied apparatus and/or device, such as for example magnetic discs, optical disks, memory, and Programmable Logic Devices (PLDs), used to provide machine instructions and/or data to a programmable data processor, including a machine-readable medium that receives machine instructions as a machine-readable signal. The term "machine-readable signal" refers to any signal used to provide machine instructions and/or data to a programmable data processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A method for implementation by one or more data processors forming part of at least one computing system, the method comprising:
    determining, by at least one data processor during monitoring of a patient, that a plurality of alarm conditions have been triggered, each alarm condition characterizing a measurement by and/or operation of at least one medical device and having an associated grade among a plurality of prioritized grades; and
    generating and conveying, by at least one data processor, audio and/or vibrational alarms corresponding to each of the plurality of alarm conditions such that among concurrent active alarms:
        an alarm corresponding to an alarm condition having a highest priority grade is conveyed at a first level and, when such alarm condition remains active for a pre-defined time period, is conveyed again at the first level upon expiration of the pre-defined time period, and
        alarms corresponding to alarm conditions having equal or lower priority grades than the priority grade of the current highest priority grade alarm condition are conveyed at a second level while the alarm condition having the highest priority grade is active, the second level being different and distinguishable from the first level.

2. The method as in claim 1, wherein when the alarm condition having the highest priority grade is removed prior to the expiration of the pre-defined time period, an alarm corresponding to an alarm condition having a next highest priority grade is conveyed at the first level and, when such alarm condition remains active for a second pre-defined time period, is conveyed at the first level upon expiration of the second pre-defined time period.

3. The method as in claim 1, wherein the alarms at the first level are different at each priority grade and the alarms at the second level are all the same.

4. The method as in claim 1, wherein the at least one medical device is selected from a group consisting of: patient monitors, anesthesia delivery platforms, ventilators, and physiological sensors.

5. The method as in claim 1, wherein the at least one medical device comprises an alarm management system.

6. The method as in claim 1, wherein, for each triggered alarm condition, a new timer is initiated which is used to determine whether such alarm condition remains active at the expiration of the pre-defined time period.

7. The method as in claim 1, wherein the at least one computing system comprises the at least one medical device.

8. The method as in claim 1, wherein the at least one computing system forms part of an alarm management system.

9. The method as in claim 1 further comprising:
    initiating, by at least one data processor, an alarm pause for a third pre-defined time period in response to user-generated input via the at least one medical device;
    wherein at least a portion of alarms initiated during the third pre-defined time period result in an attention alarm being conveyed to a caregiver.

10. The method as in claim 9, wherein alarms initiated during the third pre-defined time period having alarm conditions at a priority grade above a pre-defined threshold are conveyed to the caregiver at the first level while all other alarms are conveyed to the caregiver at the second level.

11. A non-transitory computer program product storing instructions which, when executed by at least one data processor, result in operations comprising:
    determining, during monitoring of a patient, that a plurality of alarm conditions have been triggered, each alarm condition characterizing a measurement by and/or operation of at least one medical device and having an associated grade among a plurality of prioritized grades; and
    generating and conveying, by at least one data processor, audio and/or vibrational alarms corresponding to each of the plurality of alarm conditions such that among concurrent active alarms:
        an alarm corresponding to an alarm condition having a highest priority grade is conveyed at a first level and, when such alarm condition remains active for a pre-defined time period, is conveyed again at the first level upon expiration of the pre-defined time period, and
        alarms corresponding to alarm conditions having equal or lower priority grades than the priority grade of the current highest priority grade alarm condition are conveyed at a second level while the alarm condition having the highest priority grade is active, the second level being different and distinguishable from the first level.

12. A system comprising:
    at least one data processor; and
    memory storing instructions which, when executed by the at least one data processor, result in operations comprising:
        determining, during monitoring of a patient, that a plurality of alarm conditions have been triggered, each alarm condition characterizing a measurement by and/or operation of at least one medical device and having an associated grade among a plurality of prioritized grades; and
        generating and conveying, by at least one data processor, audio and/or vibrational alarms corresponding to each of the plurality of alarm conditions such that among concurrent active alarms:
            an alarm corresponding to an alarm condition having a highest priority grade is conveyed at a first level and, when such alarm condition remains active for a pre-defined time period, is conveyed again at the first level upon expiration of the pre-defined time period, and
            alarms corresponding to alarm conditions having equal or lower priority grades than the priority grade of the current highest priority grade alarm condition are conveyed at a second level while the alarm condition having the highest priority grade is active, the second level being different and distinguishable from the first level.

13. A system comprising:
    at least one sensor for characterizing aspects of a patient;
    at least one medical device in communication with the at least one sensor, the at least one medical device triggering a plurality of alarm conditions, each alarm condition characterizing a measurement by and/or operation of the at least one medical device and having an associated grade among a plurality of prioritized grades; and an alarm management system coupled to the at least one medical device, the alarm management system comprising at least one data processor that determines, during monitoring of the patient, that a plurality of alarm conditions have been triggered and generating and conveying audio and/or vibrational alarms corresponding to each of the plurality of alarm conditions such that among concurrent active alarms:

an alarm corresponding to an alarm condition having a highest priority grade is conveyed at a first level and, when such alarm condition remains active for a pre-defined time period, is conveyed again at the first level upon expiration of the pre-defined time period, and alarms corresponding to alarm conditions having equal or lower priority grades than the priority grade of the current highest priority grade alarm condition are conveyed at a second level while the alarm condition having the highest priority grade is active, the second level being different and distinguishable from the first level.

14. The system as in claim 13, wherein when the alarm condition having the highest priority grade is removed prior to the expiration of the pre-defined time period, an alarm corresponding to an alarm condition having a next highest priority grade is conveyed at the first level and, when such alarm condition remains active for a second pre-defined time period, is conveyed at the first level upon expiration of the second pre-defined time period.

15. The system as in claim 13, wherein the alarms at the first level are different at each priority grade and the alarms at the second level are all the same.

16. The system as in claim 13, wherein the at least one medical device is selected from a group consisting of: patient monitors, anesthesia delivery platforms, ventilators, and physiological sensors.

17. The system as in claim 13, wherein the at least one medical device comprises an alarm management system.

18. The system as in claim 13, wherein the at least one data processor of the alarm management system initiates an alarm pause for a third pre-defined time period in response to user-generated input via the at least one medical device;

wherein at least a portion of alarms initiated during the third pre-defined time period result in an attention alarm being conveyed to a caregiver.

19. The system as in claim 13, wherein alarms initiated during the third-pre-defined time period having alarm conditions at a priority grade above a pre-defined threshold are conveyed to the caregiver at the first level while all other alarms are conveyed to the caregiver at the second level.

20. The system as in claim 13, wherein for each triggered alarm condition, a new timer is initiated which is used to determine whether such alarm condition remains active at the expiration of the pre-defined time period.

* * * * *